United States Patent
Dougherty

(12) 
(10) Patent No.: US 6,180,804 B1
(45) Date of Patent: Jan. 30, 2001

(54) REVERSION OF EXPOXIDE IN THE PRODUCTION OF HYDROGEN PEROXIDE

(75) Inventor: Edward F. Dougherty, League City, TX (US)

(73) Assignee: FMC Corporation, Philadelphia, PA (US)

( * ) Notice: Under 35 U.S.C. 154(b), the term of this patent shall be extended for 0 days.

(21) Appl. No.: 09/151,145

(22) Filed: Sep. 10, 1998

(51) Int. Cl.$^7$ .............................. C07C 46/00; C07C 50/18
(52) U.S. Cl. ............................ 552/268; 552/296
(58) Field of Search ..................... 552/296, 208

(56) References Cited

U.S. PATENT DOCUMENTS

| | | | |
|---|---|---|---|
| 2,636,057 | 4/1953 | Cutcher et al. | 260/682 |
| 2,739,875 | 3/1956 | Sprauer et al. | 23/207 |
| 3,330,625 | 7/1967 | Baker et al. | 23/207 |
| 3,432,267 | 3/1969 | Lee et al. | 23/207 |
| 3,565,581 | 2/1971 | Lee | 23/207 |
| 3,767,778 | 10/1973 | Glasselmann | 423/588 |
| 3,767,779 | 10/1973 | Colngt | 423/588 |
| 3,780,168 | 12/1973 | Kabisch | 423/588 |
| 3,912,766 | 10/1975 | Logan et al. | 260/369 |
| 3,965,251 | 6/1976 | Shin et al. | 423/588 |
| 4,529,827 | 7/1985 | Drake | 585/640 |
| 4,566,998 | 1/1986 | Ochoa et al. | 260/369 |
| 4,668,436 | 5/1987 | Sethi | 260/369 |
| 4,824,609 | 4/1989 | Sethi | 260/369 |
| 4,946,666 | 8/1990 | Brown | 423/625 |

FOREIGN PATENT DOCUMENTS

| | | |
|---|---|---|
| 608824 | 11/1960 | (CA) . |
| 798237 | 7/1958 | (GB) . |
| 1004371 | 9/1965 | (GB) . |

OTHER PUBLICATIONS

"Hydrogen Peroxide," in Kirk–Othmer Encyclopedia of Chemical Technology, 3rd ed, vol. 13, Wiley, New York, 1981, pp. 12–22.

"Aluminum Compounds," in Kirk–Othmer Encyclopedia of Chemical Technology, 4th ed, vol. 2, Wiley, New York, 1992, pp. 252–253;291–293;317–323.

"Aluminum Oxide," in Ullman's Encyclopedia of Industrial Chemistry, 5th ed, vol. A1, VCH, Weinheim, 1985, pp. 557–563;587–592.

*Primary Examiner*—John Kight
*Assistant Examiner*—Raymond Covington
(74) *Attorney, Agent, or Firm*—Bruce M. Monroe; Patrick C. Baker

(57) ABSTRACT

A working solution for producing hydrogen peroxide, containing an alkylanthraguinone working compound dissolved in a solvent, is regenerated by contacting the working solution with a catalyst containing from 5% to 100% boehmite at a temperature of 25° C. to 150° C. At least a portion of the tetrahydro-alkylanthraquinone epoxide present in the working solution is converted to working compound to maintain the composition of the working solution within specified limits.

14 Claims, No Drawings

REVERSION OF EXPOXIDE IN THE PRODUCTION OF HYDROGEN PEROXIDE

TECHNICAL FIELD

This invention relates to the anthraquinone process for the manufacture of hydrogen peroxide. More particularly, the invention is a process for regenerating a working solution used in the preparation of hydrogen peroxide in which tetrahydro-alkylanthraquinone epoxide is converted to working compound using a boehmite catalyst.

BACKGROUND

The anthraquinone process (also called the autoxidation process or the Riedl-Pfleiderer process) for the manufacture of hydrogen peroxide ($H_2O_2$) is well known. It is described, for example, in Riedl, U.S. Pat. No. 2,158,525, and in the *Kirk-Othmer Encyclopedia of Chemical Technology*, 3rd. ed., Volume 13, Wiley, New York, 1981, pp. 15–22. The process is shown schematically below.

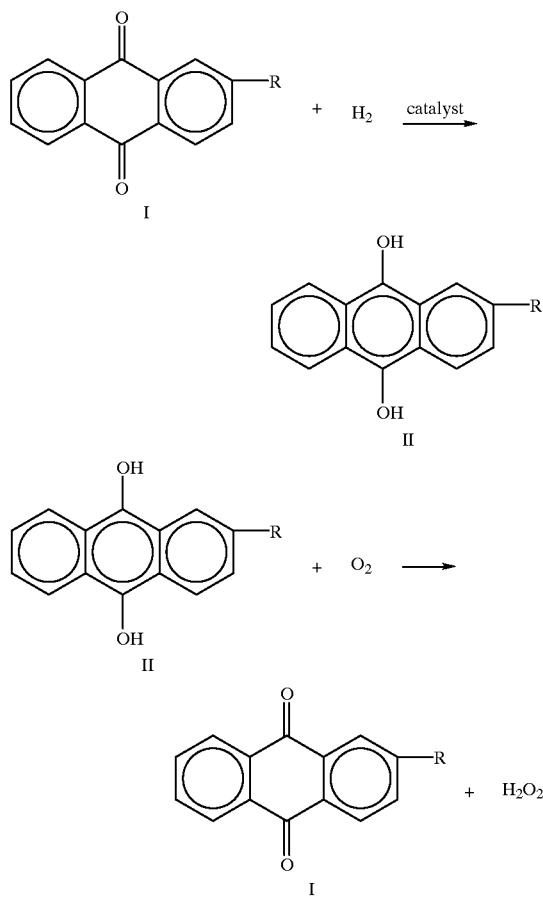

In this process, an alkyl-substituted anthraquinone (I), preferably a 2-alkylanthraquinone, known as a working compound, is dissolved in a suitable solvent or solvent mixture to form a working solution. The working solution is catalytically reduced to form the corresponding dihydroanthraquinone (II). The dihydroanthraquinone is separated from the hydrogenation catalyst and exposed to an oxygen-containing gas, usually air, to produce hydrogen peroxide and reform the anthraquinone (I). The hydrogen peroxide is extracted from the solvent with water, purified, and concentrated. The extracted solvent is recycled to the hydrogenation step to reform the dihydroanthraquinone (II) and continue the process.

During the hydrogenation and oxidation steps the working compound can undergo a number of secondary reactions. Reduction of one of the aromatic rings produces a tetrahydro-anthraquinone (III). Although the tetrahydro-anthraquinone is effective in producing hydrogen peroxide and is considered to be part of the working compound, it is the apparent precursor of a tetrahydro-anthraquinone epoxide (IV). The tetrahydro-anthraquinone epoxide is ineffective in producing hydrogen peroxide. It builds up in the working solution as the working solution is recycled through the process. Eventually it must be converted to working compound or removed to maintain the composition of the working solution within prescribed limits.

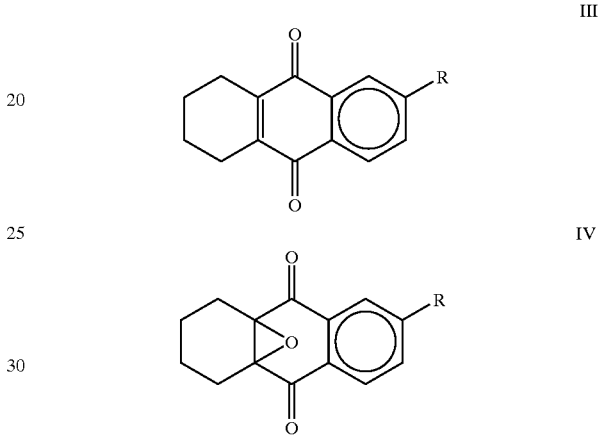

Numerous processes for regenerating the working solution have been disclosed. For example, Sprauer, U.S. Pat. No. 2,739,875, discloses regenerating the working solution by heating it with either activated alumina or activated magnesia. Logan, U.S. Pat. No. 3,912,766, discloses that a degraded working solution may be regenerated by subjecting the solution to at least two different regeneration agents differing in at least one significant characteristic. The treatments suggested included activated alumina for the hydro (reduced) phase, and aqueous sodium hydroxide for the neutral (oxidized) phase. Shin, U.S. Pat. No. 3,965,251, discloses regenerating a working solution by contacting it at 130° C. or higher with a platinum metal and an olefinic compound whose hydrogenation compound is gaseous at the operating temperature. Ochoa, U.S. Pat. No. 4,566,998, discloses a process for regenerating a mixed oxidized and hydrogenated working solution with an alkaline, activated alumina containing sodium oxide at 145° C.

Although the epoxide can be converted back to working compound, these conversions are not quantitative; usually there is a significant loss of working compound. Because anthraquinone is expensive, this loss is a significant expense in the process. In addition, the epoxide is usually converted to working compound in the hydro phase or reduced phase (after hydrogenation), but dehydrogenation of tetrahydro-anthraquinone to the anthraquinone usually takes place in the neutral, or oxidized, phase (before hydrogenation) so that it necessary to treat both phases of the process. Thus, a need exists for a better method for converting tetrahydro-anthraquinone epoxide to working compound and which, preferably, also converts the tetrahydro-anthraquinone to the corresponding anthraquinone, so that it is only necessary to treat one phase of the process.

DISCLOSURE OF THE INVENTION

The invention is a process for regenerating a working solution used in the preparation of hydrogen peroxide in which tetrahydro-alkylanthraquinone epoxide is converted to working compound using a boehmite catalyst. More particularly, the invention is a process for regenerating a working solution used in the preparation of hydrogen peroxide, the working solution comprising working compound, a solvent, and a tetrahydro-alkylanthraquinone epoxide, the process comprising contacting the working solution with a catalyst comprising from 5% to 100% boehmite at a temperature of 25° C. to 150° C., whereby at least a portion the tetrahydro-alkylanthraquinone epoxide is converted to working compound.

As a result of this treatment at least part of the tetrahydro-alkylanthraquinone epoxide is converted to working compound. In addition, part of the tetrahydro-alkylanthraquinone is dehydrogenated to the alkylanthraquinone. The method is preferably carried out in the hydro phase, i.e., after reduction of the working solution, but before oxidation of the working solution.

Working Solution

The working solution comprises the working compound and the solvent. The working compound includes the alkylanthraquinone as well as those products formed from the alkylanthraquinone during the reduction and oxidation steps that are effective in producing hydrogen peroxide. Reaction products that are not effective in producing hydrogen peroxide are not considered to be part of the working compound. Although the chemical yield of hydrogen peroxide per cycle is high, these reaction products, known as inerts, build up in the working solution as the working solution is recycled through the process. Eventually these compounds must be either converted to working compound or removed to maintain the composition of the working solution within its prescribed limits.

Alkylanthraquinones suitable for use as the working compound are substituted with an alkyl group, preferably an alkyl group of one to six carbon atoms, on a position not immediately adjacent to the quinone ring (i.e., the 2-, 3-, 6-, or 7-position). These include 2-ethylanthraquinone, 2-isopropylanthraquinone, 2-sec-butylanthraquinone, 2-tert-butylanthtraquinone, 2,5-butylanthraquinone, 2-sec-amylanthraquinone, 2-methylanthraquinone and 1,3-dimethylanthraquinone, as well as other alkylanthraquinones known in the hydrogen peroxide art. Preferred alkylanthraquinones are 2-ethylanthraquinone, 2-tert-butylanthraquinone, and 2-amylanthraquinone. A more preferred alkylanthraquinone is 2-ethylanthraquinone.

During the reduction and oxidation steps the anthraquinone can undergo a number of secondary reactions. Reduction of one of the aromatic rings produces 5,6,7,8-tetrahydro-anthraquinone (III). The tetrahydroanthraquinone is also effective in producing hydrogen peroxide and is considered to be part of the working compound.

The maximum capacity of the working solution for a continuous flow process is limited by the solubility of the working compound in either its reduced or oxidized state. The solubility is, in part, dependant on the alkyl substituent on the alkylanthraquinone and the solvent system. Typically the maximum working compound solubility is a eutectic mixture of the alkylanthraquinone and the tetrahydroalkylanthraquinone. Therefore, for optimum process operation, the composition of the working solution must be maintained within prescribed limits.

The solvent must have a high partition coefficient for hydrogen peroxide with water so that hydrogen peroxide can be efficiently extracted. It should be chemically stable to the process condition, insoluble or nearly insoluble in water, and a good solvent for the alkylanthraquinone in both its oxidized and reduced forms. For safety reasons, the solvent should have a high flash point, have a low volatility, and be nontoxic. Mixed solvents may be used to enhance the solubility of the anthraquinone working compound in both its hydrogenated (reduced) form, i.e., the hydroquinone form, and its oxidized (neutral) form, i.e., the quinone form.

Typical solvents used in working solutions are set forth in Glasselmann, U.S. Pat. No. 3,767,778, incorporated herein by reference, and include benzene, alkyl benzene, 1-methylnaphthalene, xylene, anisol and tert-butyltoluene as quinone solvents, and C7–C12 alcohols, methyl cyclohexyl acetate, di-iso-butyl carbinol, phosphoric acid esters, and tetra-substituted ureas as the hydroquinone solvents.

The tetrahydro-anthraquinone is the apparent precursor of tetrahydro-anthraquinone epoxide (IV). The tetrahydro-anthraquinone epoxide is ineffective in producing hydrogen peroxide, so its formation results in a loss of working compound. Although only a small amount of tetrahydro-anthraquinone epoxide is formed per cycle, tetrahydro-anthraquinone epoxide accumulates as the working solution is recycled many times. Eventually it must be either removed or regenerated to working compound to maintain the composition of the working solution within the prescribed limits.

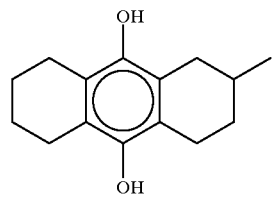

V

The working solution also contains other products formed by secondary reaction of the anthraquinone and tetrahydro-anthraquinone, such as the 1,2,3,4,5,6,7,8-octahydro-anthrahydroquinone (V), which is not effective in producing hydrogen peroxide.

Boehmite

Boehmite (α-aluminum oxide hydroxide) (CAS 1318-23-6), AlO(OH), is a naturally occurring compound of aluminum. Although sometimes referred to as an "alumina monohydrate," is generally believed an oxide hydroxide of aluminum. At lower temperatures and pressures, boehmite is the kinetically favored form of aluminum oxide hydroxide. Above about 275° C., boehmite is converted to diaspore (β-aluminum oxide hydroxide), another form of aluminum oxide hydroxide. Diaspore is converted to aluminum oxide at higher temperatures.

Boehmite is the main constituent of bauxite deposits of Europe. Hydrothermal transformation of gibbsite (α-aluminum trihydroxide) at temperatures above 150° C. is a common method for the synthesis of well-crystallized boehmite. Boehmite can be precipitated at temperatures above 100° C. from the caustic aluminate liquors used in the Bayer process for the production of alumina from bauxite. A process for the production of fine, tabular boehmite crystals from Bayer process liquor is disclosed, for example, in Brown, U.S. Pat. No. 4,946,666.

Boehmite is typically used as a pigment or filler in paper, paint and ink applications and is normally considered to be merely a precursor of activated alumina. Boehmite must be heated to over 300° C. before it is converted to an activated alumina, such as γ-alumina, δ-alumina, θ-alumina, or α-alumina, which is useful as a catalyst. Thus, it is unexpected that boehmite converts tetrahydro-alkylanthraquinone epoxide to working compound.

Aluminum oxide containing the boehmite can be used for the dehydrogenation reaction. However, if a physical mixture of aluminum oxide and boehmite is used, the boehmite may separate from the aluminum oxide and plug the process.

Manufacturing Process

The working compound is typically reduced to the hydro phase in a hydrogenator. Reduction is typically carried out at slightly elevated hydrogen partial pressure below 100° C., typically about 40° to 50° C. The degree of hydrogenation (conversion of quinone to hydroquinone) may be less than 100%, for example about 50% to 80%, to minimize formation of secondary reaction products. To maximize process economics, the reduced yield of hydrogen peroxide per cycle caused by partial hydrogenation must be balanced against the loss of working compound caused by higher amounts of hydrogenation.

The catalyst should be active, selective, stable, and have a long life. Raney nickel, the original catalyst, is active, but is pyrophoric and causes excessive ring hydrogenation. Palladium, which can be used as palladium black, as a wire screen, or supported on a carrier for slurry or fixed-bed, avoids the problems associated with Raney nickel. The hydro phase (hydrogenated working solution), free of catalyst, is oxidized with an oxygen-containing gas in an uncatalyzed reaction to form hydrogen peroxide and reform the anthraquinone. Air is typically used as the source of oxygen. The hydrogen peroxide can be extracted with water from the solution from the oxidation step using extraction techniques well-known to those skilled in the art.

The boehmite can be contacted with the working solution by any convenient means, such as in a fluid bed or in a counter current tower. Contacting can be accomplished continuously or intermittently by treating the entire plant stream, treating a portion in a sidestream, or batchwise by withdrawing a portion of the working solution. A preferred procedure involves continuously treating a portion, e.g., about 10%, of the working solution in a sidestream. In this manner buildup of the epoxide in the working solution is avoided and the composition of the working solution can be maintained. Contacting can be carried out at about 25° C. to about 150° C.

The contacting may be carried out in either the neutral phase (after extraction of the hydrogen peroxide, but before hydrogenation), the hydra phase (after hydrogenation), or both. Contacting in the hydro phase increases the concentration of the tetrahydro-anthraquinone and, thus, helps to maintain the preferred ratio of tetrahydro-anthraquinone to anthraquinone. Consequently, it is preferred that working solution in the hydro phase be contacted with boehmite.

INDUSTRIAL APPLICABILITY

This process of the invention converts tetrahydro-alkylanthraquinone epoxide to working compound during the manufacture of hydrogen peroxide. Hydrogen peroxide is widely used a non-polluting oxidizing agent and as well as in the manufacture of other peroxygen compounds, such as Caro's acid (peroxymonosulfuric acid), sodium percarbonate, sodium perborate, and percarboxylic acids such as peroxyacetic acid.

The advantageous properties of the invention can be observed by reference to the following examples which illustrate, but do not limit, the invention.

EXAMPLES

Although the invention does not depend upon any particular theory of operation, it is convenient to explain the invention in terms of a reaction scheme in which the tetrahydro-alkylanthraquinone epoxide (IV) is converted to working compound in steps. In the first step the epoxy ring is opened by hydrogenation to form the corresponding alcohol (VI). In a subsequent step the alcohol is dehydrated to the tetrahydro-alkylanthraquinone (III).

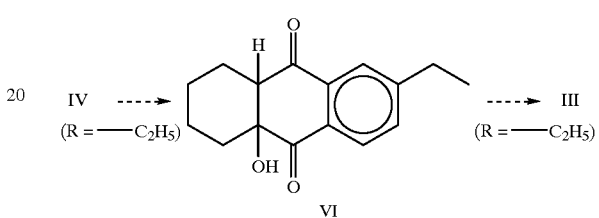

Although the invention has been illustrated using 2-ethylanthraquinone and its derivatives, any alkylanthraquinone useful for the production of hydrogen peroxide may be used in the practice of the invention.

| Glossary | |
|---|---|
| EAQ | 2-Ethylanthraquinone (I; R = —C$_2$H$_5$) |
| H4EAQ | Tetrahydro-2-ethylanthraquinone (III; R = —C$_2$H$_5$) |
| H4EAQ-EO | Tetrahydro-2-ethylanthraquinone epoxide (IV; R = —C$_2$H$_5$) |
| EA | Alcohol formed by catalytic hydrogenation of tetrahydro-2-ethylanthraquinone epoxide (VI) |

All concentrations are by weight unless otherwise specified.

Example 1

This example shows the preparation of EA, the alcohol (VI) formed by catalytic hydrogenation of tetrahydro-2-ethylanthraquinone epoxide.

A sample of tetrahydro-ethylanthraquinone epoxide (H4EAQ-EO) was dissolved in methanol and hydrogenated in the presence of palladium on a barium sulfate catalyst to produce the alcohol formed by opening the epoxy ring. Hydrogenation was carried out at −5° C. and about 1 atmosphere of hydrogen. The resulting product can be washed with hexane to produce a relatively pure product that contains a small amount of H4EAQ. Catalysts other than palladium on barium sulfate did not produce the desired product in acceptable yields.

Example 2

This example shows that boehmite converts over 37% of the epoxy alcohol (EA) to working compound (EAQ+ H4EAQ), a far greater percentage than any other of the alumina-containing compounds examined.

EA was made up as a 1% by weight stock solution in a solvent consisting of 79% n-heptane and 20% tri-octal phosphate. A series of 25 mL aliquots of the stock solution was reacted in a laboratory back mixed reactor with different catalysts for 4 hr at 70° C. Each sample was analyzed by liquid chromatography to identify the alcohol (EA) remaining, as well as the ethylanthraquinone (EAQ) and the tetrahydro-ethylanthraquinone (H4EAQ) formed. The results are shown in Table 1.

TABLE 1

Effect of Catalyst on Epoxy Alcohol Formation[a]

| CATALYST | % EA | % EAQ | % H4EAQ |
|---|---|---|---|
| Boehmite[b] | 1.73 | 14.43 | 23.02 |
| Gamma Alumina[b] | 62.31 | 0.60 | 7.63 |
| Neutral Alumina[c] | 55.47 | 0.00 | 3.54 |
| Basic Alumina[c] | 58.00 | 0.61 | 7.42 |
| Acidic Alumina[c] | 70.56 | 0.19 | 4.26 |
| Aluminum Hydroxide | 100 | 0.00 | 0.00 |
| Kaolin[c] | 100 | 0.00 | 0.00 |
| Bayerite[d] | 100 | 0.00 | 0.00 |
| Desiccant Grade Alumina[e] | 80 | 0.56 | 1.23 |
| Zeolite (Mixture)[c] | — | — | — |
| Aluminum Oxide 99% Alpha[c] | 83 | — | 0.33 |
| Alumina 103 EI[f] | 25 | 0.47 | 2.48 |

[a]After 4 hr at 70° C.
[b]From Discovery Alumina.
[c]From Aldrich Chemical Company.
[d]From LaRoche.
[e]From Sigma.
[f]From Universal Scientific.

Example 3

This example shows conversion of the epoxy alcohol (EA) to working compounds (EAQ+H4EAQ) as a function of time using boehmite and gamma-alumina as catalysts.

The procedure of Example 2 was repeated using boehmite and gamma-alumina as catalysts. Samples were analyzed at various times. The results are shown in Tables 2 and 3.

TABLE 2

Boehmite Catalyst

| TIME (hr) | % EA | % EAQ | % H4EAQ |
|---|---|---|---|
| 0 | 100 | — | — |
| 0.5 | 15.9 | 0.24 | 4.76 |
| 1 | 14.9 | 0.51 | 10.3 |
| 2 | 10.6 | 2.69 | 17.07 |
| 4 | 4.9 | 9.23 | 23.83 |
| 8 | 2.8 | 23.76 | 16.08 |
| 24 | 0.7 | 32.45 | 13.29 |

TABLE 3

Gamma-Alumina

| TIME (hr) | % EA | % EAQ | % H4EAQ |
|---|---|---|---|
| 0 | 100 | — | — |
| 1 | 43.0 | 0.25 | 1.54 |
| 2 | 47.0 | 0.23 | 2.07 |
| 4 | 59.4 | 0.32 | 3.30 |
| 8 | 62.3 | 0.60 | 4.40 |
| 24 | 43.2 | 2.62 | 15.74 |

Example 4

Because commercial grades of boehmite are available only as fine powders, this experiment was carried out to determine whether alumina could be doped with varying amounts of boehmite and used in a granular form. The catalysts were made by adding boehmite to an alumina substrate in varying amounts, extruding the mixture, drying the extrudate, and screening the extrudate to an 8×20 mesh.

The samples were evaluated by determining the percentage reversion of a 1% solution of the H4EAQ-EO to H4EAQ in a solution of 20% trioctal phosphate and 79% n-hexane at 60° C. for up to 7 hr in the absence of hydrogen (neutral phase). The results are presented in Table 4.

TABLE 4

| BOEHMITE (%)[a] | % H4EAQ-EO | % EAQ | % H4EAQ |
|---|---|---|---|
| 0 | 56.3 | 11.2 | 0.4 |
| 5 | 11.0 | 42.3 | 3.7 |
| 10 | 45.5 | 20.5 | 19.5[b] |
| 20 | 36.3 | 21.5 | 1.2 |
| 30 | 35.5 | 21.2 | 1.6 |
| 40 | 9.0 | 39.4 | 1.9 |
| 50 | 6.3 | 40.5 | 2.7 |
| 100 | 0.0 | 65.0 | 0.1 |

[a]Physical mixture of boehmite and alumina DD-6 (Discovery).
[b]This value is probably incorrect.

These results are surprising in that the primary product after 420 min (7 hr) is not H4EAQ but EAQ, suggesting that the hydrogen needed to open the epoxy ring can be provided by dehydrogenating the H4EAQ.

Example 5

This example shows the boehmite catalyzed reversion of H4EAQ and H4EAQ-EO to EAQ in the neutral phase, i.e., after extraction of the hydrogen peroxide, but before hydrogenation. Complete reversion of H4EAQ-EO was observed in all but one experiment. In addition, in every experiment part of the H4EAQ-EO was converted to EAQ.

The procedure of Example 4 was repeated using a neutral phase plant working solution from which the hydrogen peroxide had been extracted. The results are presented in Table 5.

TABLE 5

| | INITIAL | | | FINAL | | |
|---|---|---|---|---|---|---|
| % BOEHMITE | % H4EAQ-EO | % EAQ | % H4EAQ | % H4EAQ-EO | % EAQ | % H4EAQ |
| 5 | 0.61 | 3.33 | 8.9 | 0 | 5.13 | 7.63 |
| 10 | 0.61 | 3.25 | 8.9 | 0 | 5.05 | 7.41 |
| 20 | 0.47 | 3.25 | 8.9 | 0.19 | 5.93 | 7.57 |
| 30 | 0.47 | 3.18 | 8.9 | 0 | 5.18 | 7.07 |
| 40 | 0.47 | 3.18 | 8.9 | 0 | 4.90 | 7.37 |
| 50 | 0.74 | 3.34 | 8.8 | 0 | 5.16 | 7.41 |

Example 6

This example illustrates that a catalyst containing 20% boehmite is more effective in converting tetrahydro-alkylanthraquinone epoxide to working compound in the hydrogenated phase than in the neutral phase.

Samples (25 mL) of plant working solution in both the hydrogenated phase and the neutral phase were contacted with 1 and 2 g of a 20% boehmite catalyst, prepared as described above, at 70° C. in a backmixed reactor. Results are presented in Table 6.

TABLE 6

| TIME (hr) | % EA | % EAQ | % H4EAQ | % Total[a] | % Quinone[b] |
|---|---|---|---|---|---|
| 1 g Catalyst - Neutral Phase | | | | | |
| 0 | 0.62 | 4.31 | 6.17 | 10.48 | 11.10 |
| 3 | 0.66 | 4.84 | 7.41 | 12.25 | 12.91 |
| 6 | 0.65 | 4.77 | 7.28 | 12.05 | 12.70 |
| 24 | 0.55 | 4.95 | 7.60 | 12.55 | 12.55 |
| 2 g Catalyst - Neutral Phase | | | | | |
| 0 | 0.62 | 4.31 | 6.17 | 10.48 | 11.10 |
| 3 | 0.58 | 4.80 | 7.42 | 12.22 | 12.80 |
| 6 | 0.50 | 4.83 | 7.37 | 12.20 | 12.70 |
| 24 | 0.00 | 5.08 | 7.29 | 12.37 | 12.37 |
| 1 g Catalyst - Hydro Phase | | | | | |
| 0 | 0.55 | 4.66 | 7.60 | 12.26 | 12.81 |
| 3 | 0.00 | 4.78 | 8.25 | 13.03 | 13.03 |
| 6 | 0.00 | 4.67 | 8.16 | 12.83 | 12.83 |
| 24 | 0.00 | 4.77 | 8.42 | 13.19 | 13.19 |
| 2 g Catalyst - Hydro Phase | | | | | |
| 0 | 0.53 | 4.59 | 7.63 | 12.22 | 12.75 |
| 3 | 0.00 | 4.71 | 8.39 | 13.10 | 13.10 |
| 6 | 0.00 | 4.70 | 8.36 | 13.06 | 13.06 |
| 24 | 0.00 | 4.40 | 7.86 | 12.26 | 12.26 |

[a] % EAQ + % H4EAQ
[b] % EA + % EAQ + % H4EAQ

With 1 g of catalyst in neutral phase working solution, there was only a small reduction in the concentration of EA. With 2 g of catalyst in neutral phase working solution, there was complete removal of EA in 24 hr. However, with either 1 g or 2 g of catalyst in the hydro phase, there was complete removal of the EA in less than 3 hr.

Having described the invention, I now claim the following and their equivalents.

What is claimed is:

1. A process for regenerating a working solution used in the preparation of hydrogen peroxide, the working solution comprising working compound, a solvent, and a tetrahydro-alkylanthraquinone epoxide, the process comprising contacting the working solution with a catalyst comprising from 5% to 100% boehmite at a temperature of 25° C. to 150° C., whereby at least a portion of the tetrahydro-alkylanthraquinone epoxide is converted to working compound.

2. The process of claim 1 in which the working compound comprises a 2-alkylanthraquinone.

3. The process of claim 2 in which the 2-alkylanthraquinone is selected from the group consisting of 2-ethylanthraquinone, 2-tert-butylanthraquinone, and 2-amylanthraquinone.

4. The process of claim 2 in which the working solution is in the hydro phase.

5. The process of claim 4 in which the 2-alkylanthraquinone is selected from the group consisting of 2-ethylanthraquinone, 2-tert-butylanthraquinone, and 2-amylanthraquinone.

6. The process of claim 2 in which the working solution is in the neutral phase.

7. The process of claim 6 in which the 2-alkylanthraquinone is selected from the group consisting of 2-ethylanthraquinone, 2-tert-butylanthraquinone, and 2-amylanthraquinone.

8. A process for regenerating a working solution used in the preparation of hydrogen peroxide, the process comprising (a) catalytically reducing a working solution, the working solution comprising working compound, a solvent, and a tetrahydro-alkylanthraquinone epoxide; (b) oxidizing the working solution with an oxygen-containing gas to form hydrogen peroxide, and (c) removing the hydrogen peroxide from the working solution;

in which at least a portion of the working solution is contacted with a catalyst comprising from 5% to 100% boehmite at a temperature of 25° C. to 150° C., whereby at least a portion the tetrahydro-alkylanthraquinone epoxide is converted to working compound.

9. The process of claim 8 in which the working solution comprises a 2-alkylanthraquinone.

10. The process of claim 8 in which the 2-alkylanthraquinone is selected from the group consisting of 2-ethylanthraquinone, 2-tert-butylanthraquinone, and 2-amylanthraquinone.

11. The process of claim 9 in which the working solution, is in the hydro phase.

12. The process of claim 11 in which the 2-alkylanthraquinone is selected from the group consisting of 2-ethylanthraquinone, 2-tert-butylanthraquinone, and 2-amylanthraquinone.

13. The process of claim 9 in which the working solution is in the neutral phase.

14. The process of claim 13 in which the alkylanthraquinone is selected from the group consisting of 2-ethylanthraquinone, 2-tert-butylanthraquinone, and 2-amylanthraquinone.

* * * * *